United States Patent

Antila

(10) Patent No.: US 6,735,070 B2
(45) Date of Patent: May 11, 2004

(54) ARTICLE FOR STATIC CHARGE DISSIPATION

(75) Inventor: Garth V. Antila, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 12 days.

(21) Appl. No.: 10/116,608

(22) Filed: Apr. 4, 2002

(65) Prior Publication Data

US 2003/0189806 A1 Oct. 9, 2003

(51) Int. Cl.⁷ .............................. H01H 47/00; H05F 3/00
(52) U.S. Cl. ......................................... 361/220; 361/223
(58) Field of Search ................................ 361/212, 220, 361/223; 52/901

(56) References Cited

U.S. PATENT DOCUMENTS

| | | |
|---|---|---|
| 4,398,277 A | 8/1983 | Christiansen et al. |
| 4,459,633 A | 7/1984 | Vandermark |
| 4,475,141 A | 10/1984 | Antonevich |
| 4,577,256 A * | 3/1986 | Breidegam .................. 361/220 |
| 4,677,521 A | 6/1987 | Frazier |
| 4,680,668 A | 7/1987 | Belkin |
| 4,698,724 A | 10/1987 | Burvee |
| 4,755,144 A | 7/1988 | Gordon et al. |
| 4,813,459 A | 3/1989 | Breidegam |
| 4,847,729 A | 7/1989 | Hee |
| 5,134,538 A | 7/1992 | Weiss |
| 5,184,274 A | 2/1993 | Weiss |
| 5,196,985 A | 3/1993 | Ford et al. |
| 5,677,822 A * | 10/1997 | Cohen et al. ............... 361/220 |
| 5,754,389 A | 5/1998 | Hsu |
| 6,215,639 B1 * | 4/2001 | Hee ........................... 361/212 |

FOREIGN PATENT DOCUMENTS

| | | |
|---|---|---|
| CH | 665073 | 4/1988 |
| WO | WO 98/00196 | 1/1998 |

* cited by examiner

*Primary Examiner*—Dean A. Reichard
*Assistant Examiner*—Eric Thomas
(74) *Attorney, Agent, or Firm*—Yen Tong Florczak

(57) ABSTRACT

An article for dissipating accumulated static charges from a substantially insulated surface. The article includes a single layer elongate conductor, having opposing ends, and at least one fastener located to join the opposing ends together to provide a continuous conductive loop in contact with the substantially insulated surface. The fastener further provides electrical connection to a ground cord for removal of accumulated static charge from the substantially insulated surface. A fastener may be either electrically conductive or electrically insulating provided it facilitates contact between the elongate conductor and a conductive portion of a ground cord.

12 Claims, 2 Drawing Sheets

ARTICLE FOR STATIC CHARGE DISSIPATION

BACKGROUND OF THE INVENTION

1. Field of the Invention

The invention relates to devices suitable for providing a pathway to ground for static charges accumulated on substantially non-conducting surfaces including portions of the human body. More particularly the present invention provides a fastening structure combining a clasp and electrical connector for a simple static dissipative wristband, worn by personnel working close to static-sensitive electronic components and assemblies, to prevent damaged in the event of discharge of accumulated static charge.

2. Discussion of the Related Art

The known sensitivity of electronic circuits to accumulated static charge creates the need for precautionary measures to eliminate static discharge events that damage electronic components and assemblies. Such measures include configuring workstations with antistatic carpet, conductive or dissipative or grounded desktop work surfaces and ion generators used to neutralize static charges. Personnel involved in manufacturing integrated circuits and microelectronic components and assemblies use grounding straps to keep themselves and their surroundings at zero electrical potential. Grounding straps may comprise a fabric band wrapped around a wrist or ankle and secured in place by a clasp or buckle or similar mechanical fastener. Wrist straps and ankle straps include means for adjustment to assure a proper fit with the wearer's limb. U.S. Pat. No. 5,184,274 illustrates several grounding strap concepts including features to ensure that the wearer's skin is electrically connected to ground. This connection typically occurs by contact with a conductive surface on the inside of a strap. The conductive surface may include a discrete conductive element or, as described in U.S. Pat. No. 4,398,277 and U.S. Pat. No. 4,813,459, a layer or distribution of conductive fibers that contact the wearer's skin. Some static-conductive wrist straps incorporate both a conductive element and conductive fibers for removing electrostatic charges via a suitable connection to ground. A connection to ground may include a separable snap connector to provide continuous electrical connection between a conductive element or conductive fibers and a wire (i.e. a ground cord) leading to ground. This arrangement of components directs accumulated static charge from a wearer to ground via the wrist strap and the ground cord. The ground cord typically has a built-in current limiting resistor to prevent electrical shocks to the wearer.

Personnel in electronics manufacturing industries have a broad array of grounding straps to choose from. Products range from expensive and durable, for multiple refuse, to low-cost grounding straps, such as that described in U.S. Pat. No. 4,698,724, which is intended for disposal after one or two uses. Expensive grounding straps comprise multiple parts including an insulating material portion having a resistance of more than $10^{14}$ ohms combined with a conductive portion with an electrical resistance of less than $10^5$ ohms. Structures for securing wrist and ankle bands are usually separate from conductive connecting elements used for attaching a ground cord. U.S. Pat. No. 4,677,521, U.S. Pat. No. 4,847,729 and U.S. Pat. No. 5,196,985 provide examples of grounding straps of the type described.

Other devices that assist in dissipation of accumulated static charge include buckles and clasps that may be used with a variety of different types of strap material. U.S. Pat. No. 4,755,144 describes a static grounding buckle for securing a conductive strap. The buckle has a conductive base for skin contact and a non-conductive cover partially attached to the base. A conductive attachment element is on the non-conductive cover and a conductive clip member is within the non-conductive cover to provide electrical continuity between the conductive base and the conductive attachment element. While not attached to the strap, the buckle may be used to secure a strap to a user's wrist or ankle by gripping the loose ends of the strap. A similar gripping device, described in CH 665,073, has two parallel metal tongues, produced by folding a metal strip. The upper tongue has a conductive stud protruding from its surface for connection of a ground wire. After wrapping a band around a limb of a user, the spring force of the tongues of the metal strip grip the loose ends of the band to secure it to the limb. This places the lower tongue of the metal strip in contact with the wrist or ankle of the user to provide a conducting path from skin to ground. Lacking connection to a band or strap, loose buckles or clasps are easily lost or misplaced. Also, buckles and clasps hold loose strap ends using clamps that are separate from connectors for ground wires.

Regardless of the large number of concepts for static dissipative products (resistance of between $10^5$ ohms and $10^9$) and antistatic products (a resistance of between $10^9$ ohms and $10^{14}$ ohms) there remains a need for grounding static control straps satisfying short-term use requirements, which have a relatively low cost without the use of loose parts.

SUMMARY OF THE INVENTION

The present invention satisfies the need for inexpensive static charge dissipating straps meeting performance needs between expensive, extended use straps and low cost disposable straps. As described herein static control wrist straps and static control ankle straps have the benefits of low cost, being substantially injection moldable and fabricated from few parts. Preferably a static charge dissipating strap has two parts or less. It is conceivable that static control straps according to the present invention may be a single-piece integral structure.

The development of designs having fewer parts contributes to reduction of manufacturing costs associated with limited lifetime products. Parts reduction according to the present invention occurred because of the discovery that a single structure acts as a fastener to secure the wristband and at the same time provides a ground cord connector. Previously disclosed charge dissipating devices required separate structures for securing a wristband and providing connection to a ground cord. As indicated above, known wrist straps and ankle straps etc. differ from the present invention by showing the need for one part to secure a strap and a separate part to connect the strap to a ground plane. Another difference is the common combination of non-conductive materials, to provide strength to a wristband, with one or more conductive materials that provide a path to ground for accumulations of electrostatic charge.

More particularly the present invention provides an article for dissipating accumulated static charges from a substantially insulated surface. The article comprises a single layer elongate conductor, having opposing ends, and at least one fastener located to join the opposing ends together to provide a continuous conductive loop in contact with the substantially insulated surface. The fastener further provides electrical connection to a ground cord for removal of accumulated static charge from the substantially insulated surface. A fastener may be either electrically conductive or electrically insulating provided it facilitates contact between the elongate conductor and a conductive portion of a ground cord.

The present invention further provides a method for removing accumulated static charge from a substantially insulated surface. Steps for removing static charge include providing a static charge removal device that has a single layer elongate conductor having opposing ends, a ground cord connected to a ground plane and at least one fastener located for joining together the opposing ends of the elongate conductor. After shaping the elongate conductor to provide a continuous conductive loop in contact with the substantially insulated surface, and using the fastener to join the opposing ends of the elongate conductor, a connection involving the ground cord and the fastener directs accumulated static charge away from the substantially insulated surface to ground.

Definitions

Terms used herein have the meanings indicated as follows:

A "single layer elongate conductor" refers to a strip of conducting material, preferably a plastic material of uniform composition that includes electrically conductive particles selected from particles consisting of metal and conductive carbon.

Terms such as "static dissipative strap" or "static control strap" or "static control band" or the like refer to single layer, elongate conductors placed in contact with substantially insulating surfaces to remove accumulation of static charges from the insulating surface. Such a strap or band may be further described in terms of a "wrist band" or "grounding strap" or "ankle strap" and related terms.

The term "ground cord" refers to an electrically conducting filament, typically including a metallic wire, having one end attached to ground and the other adapted for connection to a static control strap or band.

Terms including, "fastener," or "connector," or "clasp" and the like may be used herein interchangeably to describe a dual function, single element used to clamp or clasp the ends of an elongate conductor or static dissipative strap while, at the same time, acting as a point of attachment for a ground cord. A dual function, single element is a distinguishing feature of the present invention preferably in the form of a rivet or stud that may be either electrically conducting or non-conducting.

The beneficial effects described above apply generally to the static control straps disclosed herein. The specific structures though which these benefits are delivered will be described in detail hereinbelow.

BRIEF DESCRIPTION OF THE DRAWINGS

The invention will now be described in greater detail in the following way of example only and with reference to the attached drawings in which.

DESCRIPTION OF THE PREFERRED EMBODIMENTS

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Figure 1:
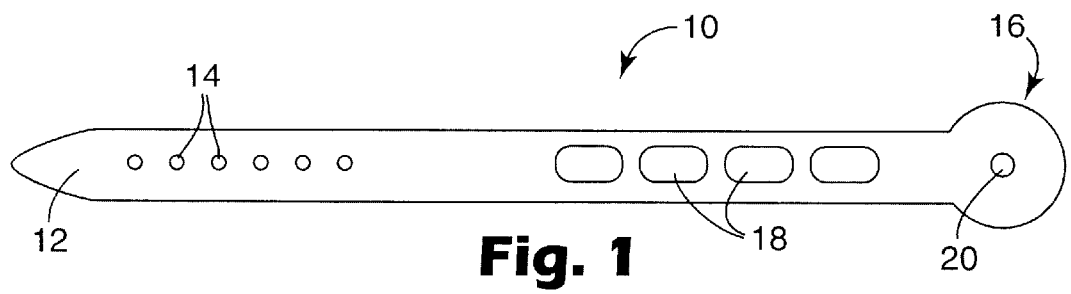
FIG. 1 is a plan view of a diagrammatic representation of a wristband according to the present invention.

Referring now the drawings wherein like numerals refer to like parts throughout the several views FIG. 1 shows an elongate strip 10 or static control strap designed to be secured to a limb of a person working with or in the vicinity of electronic components or assemblies that are known to be sensitive to electrostatic discharge. The elongate strip 10 provides a wristband or ankle strap that may be secured to the limb for attachment to a conductive ground cord, or wire, or tether or similar related device. Preferably the material of the wristband has a suitable level of electrical conductivity to release accumulated static charge to an attached ground cord.

The elongate strip 10 has a tongue extension 12 at one end. Perforations adjacent to the tongue extension 12 form a row of holes 14 parallel to the longitudinal axis of the strip 10 extending from the tongue extension 12 towards the middle of the elongate strip 10. The elongate strip 10 includes a fastener 16 positioned at the end of the strip 10 opposite to the tongue extension 12. A static dissipative strap 10 may be a one-piece molded structure having a fastener 16 integrally formed therein. Between the fastener 16 and the row of holes 14 the elongate strip 10 includes at least one opening 18, but preferably several openings, that add flexibility and extensibility to the static control strap 10.

The fastener 16 of the elongate strip 10 includes a post 20 sized to pass with difficulty through a hole in the row of holes 14. Due to its snug fit in a hole 14 the post 20 acts as a clasp to hold the tongue extension 12 against the fastener 16 end of the elongate strip 10 during formation of a circular band that acts, for example, as a wristband. As well as providing a means to secure the tongue extension 12 to the fastener 16, the post 20 provides a point for connecting a static control wristband to a ground cord accessory used to conduct electrostatic charges away from the vicinity of the elongate strip 10.

Figure 2:
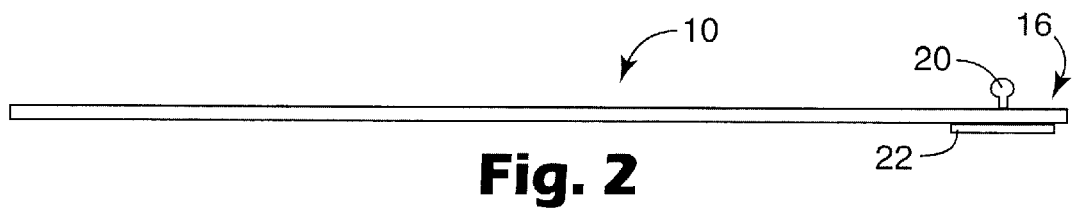
FIG. 2 is a side elevation of one embodiment of a wristband that includes a fastener as a combined clasp and electrical connector.

FIG. 2 provides a side view of an elongate strip 10 according to the present invention showing it to be a single layer of material having a fastener 16 inserted at one end. The fastener 16 includes a base 22 supporting the post 20 that has been inserted through the end of the elongate strip 10 to extend from the side of the strip 10 opposite that in contact with the base 22.

Materials used to fabricate an elongate strip 10 have sufficiently low electrical resistance to provide a conductive path for dissipation of an accumulation of electrostatic charges. Suitable materials that may be formed into elongate strips according to the present invention include inherently conductive materials including metals, plastics filled with conductive materials such as metal particles, metal fibers, conductive carbons and the like, and woven and non-woven fibrous materials that include conductive fibers or particles of the types previously described.

Figure 3:
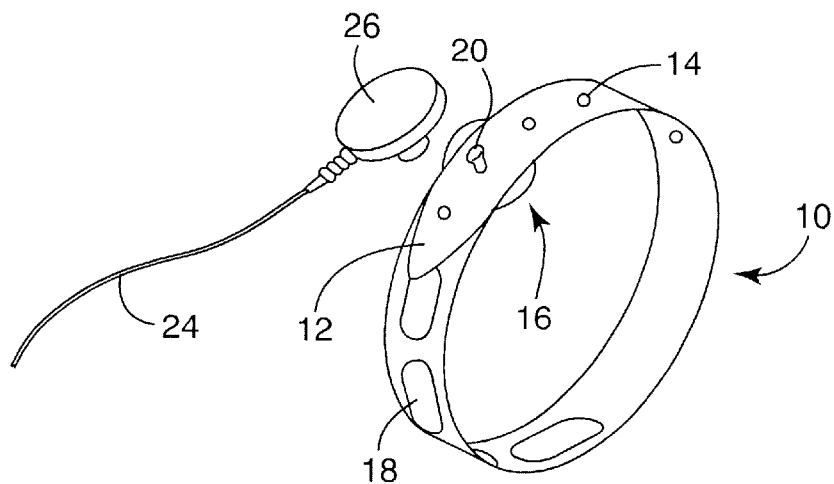
FIG. 3 provides an exploded perspective view showing one end of a wristband secured to its opposite end to form a continuous static control band positioned for connection to a cord that provides conduction of static charge from the wristband to ground.

FIG. 3 illustrates formation of a circular band, e.g. a wristband, using an elongate conductive strip 10 having its opposite ends in contact to form an electrically conductive loop held together by positioning of the post 20 of a fastener 16 through one of the holes 14 adjacent to the tongue extension 12. A fastener 16 according to the present invention may be a separate component, as previously described. As an alternative, the fastener 16 may be replaced by a means of fastening integrally formed with an elongate strip 10. Any one of a wide selection of known mechanical fastening means may be molded at one or both ends of an elongate static control strap of the present invention to provide connection that holds the elongate strip 10 in the form of a circular band. It will be appreciated that, due to the relatively low electrical resistance of an elongate strip 10, a fastener 16 according to the present invention may be electrically conducting or electrically insulating. A circular band formed from an elongate strip 10, using a fastener 16 as a clasp and connector, provides a continuous conductive path as long as there is contact between the ends of the strip 10. Conduction of electrostatic charges to ground using a wristband according to the present invention requires contact of the conductive elongate strip with a conductive portion of a cord 24 or tether that leads to ground. A preferred ground cord 24 includes a contact 26 having a conducting surface abutting the surface of the elongate strip 10 after attachment of the contact 26 using attachment means, including the preferred post 20.

Figure 4:
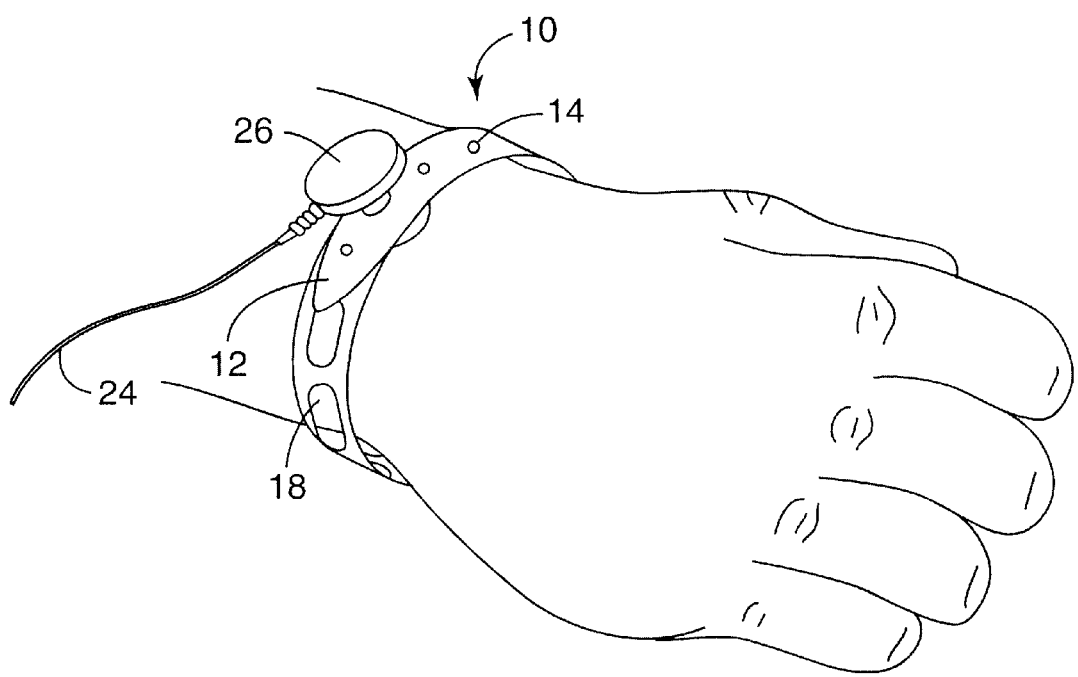
FIG. 4 shows a perspective view to illustrate attachment of a wristband according to the present invention applied to a limb of an operator to remove accumulated static charge from the body of the operator.

FIG. 4 shows a preferred use of an elongate conductive strip 10 for removing build-up of static charge from a human body, particularly from the body of a person working with sensitive electronic components and related equipment. As illustrated an elongate strip 10 provides a conductive static control band adjusted to grip a person's wrist to provide electrical continuity between the person's skin and the material of the elongate strip 10. Attachment of a contact 26 to a fastener (not shown), that retains the elongate strip 10 in loop-form, places the conductive surface of the contact 26 against the conductive wristband, thereby allowing any accumulated static charge to leak via the ground cord 24 to ground.

A static control article, formable into a conductive band, and its components have been described herein. These and other variations, which will be appreciated by those skilled in the art, are within the intended scope of this invention as claimed below. As previously stated, detailed embodiments of the present invention are disclosed herein; however, it is to be understood that the disclosed embodiments are merely exemplary of the invention that may be embodied in various forms.

What is claimed is:

1. An article for dissipating accumulated static charges from a substantially insulated surface said article comprising:
   a single layer elongate conductor having opposing ends; and
   a fastener located for joining together said opposing ends to provide a continuous conductive loop in contact with the substantially insulated surface, said fastener further providing electrical connection including contact of said elongate conductor with a ground cord for removal of accumulated static charge from the substantially insulated surface.

2. The article of claim 1, wherein said fastener is electrically conductive.

3. The article of claim 1, wherein said fastener is electrically insulating.

4. An article for dissipating accumulated static charges from a substantially insulated surface said article consisting essentially of:
   a single layer elongate conductor having opposing ends; and
   a fastener located for joining together said opposing ends to provide a continuous conductive loop in contact with the substantially insulated surface, said fastener further providing a point of connection for a ground cord to remove accumulated static charge from the substantially insulated surface.

5. An adjustable, static dissipative strap for attachment to a limb to remove accumulated electrostatic charge therefrom, said strap comprising:
   a single layer elongate conductor having a first end opposite a second end;
   a dual purpose fastener at said first end of said elongate conductor as a means for joining said first end to said second end, said dual purpose fastener further providing connection for a ground cord;
   a plurality of holes formed at said second end of said elongate conductor for attaching said second end to said dual purpose fastener to provide a continuous conductive loop having size adjustment depending upon selection of one of said plurality of holes to engage said dual purpose fastener; and
   a plurality of openings formed between said first end and said second end to allow stretching of said elongate conductor to produce gripping contact of the conductive loop encircling the limb after wrapping said elongate conductor around the limb and joining said first end to said second end.

6. The adjustable, static dissipative strap of claim 5, wherein said fastener is electrically conductive.

7. The adjustable, static dissipative strap of claim 5, wherein said fastener is electrically insulating.

8. The adjustable static dissipative strap of claim 5, formed as a one-piece molded structure.

9. The adjustable static dissipative strap of claim 5, wherein said single layer elongate conductor comprises a plastic film.

10. The adjustable static dissipative strap of claim 9, said plastic film including conductive filler.

11. A device for conducting accumulated static charge from a substantially insulated surface to ground, said device comprising:
    a single layer elongate conductor having opposing ends;
    a ground cord connected to a ground plane; and
    a fastener located for joining together said opposing ends of said elongate conductor to provide a continuous conductive loop in contact with the substantially insulated surface, said fastener providing direct connection for said ground cord to conduct accumulated static charge from the substantially insulated surface to ground.

12. A process for removing accumulated static charge from a substantially insulated surface comprising the steps of:
    providing a static charge removal device comprising:
      a single layer elongate conductor having opposing ends;

a ground cord connected to a ground plane; and a fastener located for joining together said opposing ends of said elongate conductor;

shaping said elongate conductor to provide a continuous conductive loop in contact with the substantially insulated surface;

joining said opposing ends using said fastener; and connecting said ground cord to said fastener to direct accumulated static charge from the substantially insulated surface to ground.

* * * * *

UNITED STATES PATENT AND TRADEMARK OFFICE
CERTIFICATE OF CORRECTION

PATENT NO. : 6,735,070 B2
DATED : May 11, 2004
INVENTOR(S) : Antila, Garth V.

It is certified that error appears in the above-identified patent and that said Letters Patent is hereby corrected as shown below:

Column 1,
Line 54, "refuse" should read -- re-use --.

Signed and Sealed this

Seventeenth Day of August, 2004

JON W. DUDAS
*Acting Director of the United States Patent and Trademark Office*